(12) United States Patent
Kutsuma

(10) Patent No.: US 11,882,995 B2
(45) Date of Patent: Jan. 30, 2024

(54) ENDOSCOPE SYSTEM

(71) Applicant: OLYMPUS CORPORATION, Tokyo (JP)

(72) Inventor: Yuji Kutsuma, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 707 days.

(21) Appl. No.: 16/525,764

(22) Filed: Jul. 30, 2019

(65) Prior Publication Data
US 2019/0350448 A1 Nov. 21, 2019

Related U.S. Application Data

(63) Continuation of application No. PCT/JP2017/032861, filed on Sep. 12, 2017.

(30) Foreign Application Priority Data

Feb. 1, 2017 (JP) .................................. 2017-017013

(51) Int. Cl.
*A61B 1/00* (2006.01)
*A61B 1/06* (2006.01)
(Continued)

(52) U.S. Cl.
CPC ...... *A61B 1/000095* (2022.02); *A61B 1/0638* (2013.01); *A61B 1/0661* (2013.01); (Continued)

(58) Field of Classification Search
None
See application file for complete search history.

(56) References Cited

U.S. PATENT DOCUMENTS 5,185,661 A * 2/1993 Ng ..................... H04N 1/603
358/515
5,289,295 A * 2/1994 Yumiba ................ H04N 1/62
358/518
(Continued)

FOREIGN PATENT DOCUMENTS

JP H05-244406 A 9/1993
JP 2002-034908 A 2/2002
(Continued)

OTHER PUBLICATIONS

International Search Report dated Dec. 12, 2017 issued in PCT/JP2017/032861.
(Continued)

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope system includes a light source that irradiates a predetermined first and second narrowband light; an imaging sensor that captures an image of return light of the first narrowband light and the second narrowband light from the subject, and generates an image signal of the image; and a processor being configured to identify a first color of a first portion and a second color of a second portion based on a difference of an optical density with respect to hemoglobin in the image signal in every frame of the image, the first portion corresponding to a bleeding area, and the second portion corresponding to an area other than the bleeding area within the subject, and correct the first color and the second color based on the identified first and second color while maintaining a color difference between the identified first and second color in a predetermined range.

8 Claims, 6 Drawing Sheets

(51) Int. Cl.
*G06T 7/13* (2017.01)
*G06T 7/12* (2017.01)
*A61B 1/04* (2006.01)
*A61B 5/00* (2006.01)

(52) U.S. Cl.
CPC ............... *G06T 7/13* (2017.01); *A61B 1/043* (2013.01); *A61B 1/0646* (2013.01); *A61B 5/489* (2013.01); *G06T 7/12* (2017.01); *G06T 2207/10024* (2013.01); *G06T 2207/10068* (2013.01); *G06T 2207/30101* (2013.01)

(56) References Cited

U.S. PATENT DOCUMENTS

| | | | | |
|---|---|---|---|---|
| 5,717,783 A * | 2/1998 | Endo | ............... | H04N 1/6033 358/518 |
| 5,742,520 A * | 4/1998 | Uchikawa | ............... | G06T 9/005 382/167 |
| 5,933,252 A * | 8/1999 | Emori | ............... | H04N 1/6058 358/518 |
| 6,987,583 B1 * | 1/2006 | Altmanshofer | ......... | H04N 9/643 358/1.9 |
| 9,801,573 B2 * | 10/2017 | Saito | ............... | G06T 11/001 |
| 9,854,996 B2 * | 1/2018 | Kuramoto | ......... | A61B 1/00009 |
| 10,368,728 B2 * | 8/2019 | Ito | ............... | A61B 1/00045 |
| 10,521,904 B2 * | 12/2019 | Teramura | ............ | G06T 7/0012 |
| 2002/0016533 A1 * | 2/2002 | Marchitto | ......... | A61B 5/0075 600/310 |
| 2003/0071895 A1 * | 4/2003 | Higuchi | ............... | H04N 7/183 348/E7.087 |
| 2003/0176768 A1 | 9/2003 | Gono et al. | | |
| 2004/0174548 A1 * | 9/2004 | Ono | ............... | H04N 1/603 358/1.9 |
| 2006/0082647 A1 * | 4/2006 | Donomae | ............ | H04N 9/643 348/E9.04 |
| 2006/0211915 A1 * | 9/2006 | Takeuchi | ............... | A61B 1/05 600/109 |
| 2009/0290017 A1 * | 11/2009 | Shibasaki | ............ | H04N 9/735 348/71 |
| 2009/0303319 A1 | 12/2009 | Sato et al. | | |
| 2010/0182414 A1 * | 7/2010 | Suzuki | ............... | H04N 9/74 348/71 |
| 2010/0265321 A1 * | 10/2010 | Minai | ............... | A61B 1/0638 348/E7.085 |
| 2010/0331624 A1 * | 12/2010 | Suzuki | ............... | G02B 26/008 600/109 |
| 2012/0179013 A1 * | 7/2012 | Saito | ............... | A61B 1/00009 600/339 |
| 2012/0179050 A1 * | 7/2012 | Saito | ............... | A61B 1/043 600/476 |
| 2012/0184812 A1 * | 7/2012 | Terakawa | ............ | A61B 1/00009 600/109 |
| 2012/0184813 A1 * | 7/2012 | Terakawa | ............ | A61B 1/0669 600/109 |
| 2013/0030268 A1 * | 1/2013 | Saito | ............... | A61B 5/1032 600/339 |
| 2013/0100310 A1 * | 4/2013 | Ebihara | ............... | H04N 5/225 348/222.1 |
| 2013/0123644 A1 * | 5/2013 | Gono | ............... | A61B 5/7221 600/476 |
| 2013/0172675 A1 * | 7/2013 | Yamazaki | ............ | A61B 1/0638 600/109 |
| 2013/0265401 A1 * | 10/2013 | Igarashi | ............... | A61B 1/0661 348/68 |
| 2013/0293693 A1 * | 11/2013 | Igarashi | ............... | A61B 1/0638 348/70 |
| 2013/0324797 A1 * | 12/2013 | Igarashi | ............... | A61B 1/043 600/109 |
| 2013/0329027 A1 * | 12/2013 | Igarashi | ............... | A61B 1/0684 348/68 |
| 2015/0105616 A1 * | 4/2015 | Igarashi | ............... | A61B 1/06 600/109 |
| 2016/0007829 A1 * | 1/2016 | Chun | ............... | A61B 1/00009 600/103 |
| 2016/0007830 A1 * | 1/2016 | Chun | ............... | G06T 7/90 600/476 |
| 2016/0239965 A1 * | 8/2016 | Kuramoto | ............... | H04N 7/18 |
| 2018/0020932 A1 * | 1/2018 | Chen | ............... | A61B 5/0261 600/479 |
| 2018/0214009 A1 * | 8/2018 | Endo | ............... | A61B 1/00009 |
| 2018/0228347 A1 * | 8/2018 | Yamamoto | ............ | A61B 5/1459 |
| 2019/0021580 A1 * | 1/2019 | Mishima | ............... | A61B 1/00 |
| 2019/0073768 A1 * | 3/2019 | Shigeta | ............... | G06T 7/0012 |
| 2021/0052150 A1 * | 2/2021 | Kubo | ............... | G02B 23/24 |
| 2021/0228068 A1 * | 7/2021 | Chiba | ............... | A61B 1/0646 |

FOREIGN PATENT DOCUMENTS

| | | |
|---|---|---|
| JP | 2007-274629 A | 10/2007 |
| JP | 2016-015995 A | 2/2016 |
| WO | WO 2008/102803 A1 | 8/2008 |
| WO | WO 2010/044432 A1 | 4/2010 |
| WO | WO 2013/042396 A1 | 3/2013 |
| WO | WO 2013/145407 A1 | 10/2013 |
| WO | WO 2013/145409 A1 | 10/2013 |

OTHER PUBLICATIONS

Japanese Notice of Reasons for Refusal dated Apr. 10, 2018 issued in JP 2018-507746.

* cited by examiner

BEFORE CORRECTION: △
AFTER CORRECTION: ○

BEFORE CORRECTION: △
AFTER CORRECTION: ○

| FIRST PORTION | PORTION IN WHICH ARTERIAL BLEEDING OCCURS OR PORTION ATTENUATED BY SALINE |
|---|---|
| SECOND PORTION | PORTION IN WHICH VENOUS BLEEDING OCCURS OR PORTION ATTENUATED BY SALINE |
| THIRD PORTION | ARTERIAL BLEEDING POINT |
| FOURTH PORTION | VENOUS BLEEDING POINT |

ENDOSCOPE SYSTEM

CROSS-REFERENCE TO RELATED APPLICATION

This application is a continuation of PCT International Application No. PCT/JP2017/032861 filed on Sep. 12, 2017, which designates the United States, incorporated herein by reference, and which claims the benefit of priority from Japanese Patent Application No. 2017-017013, filed on Feb. 1, 2017, incorporated herein by reference.

BACKGROUND

The present disclosure relates to an image processing apparatus, an endoscope system, an image processing apparatus operating method, and a computer readable recording medium.

In the past, an endoscope system has been used in the medical field to observe a living tissue inside a subject. In the endoscope system, a technique for emphasizing an observation target, such as a living tissue, to improve visibility of the observation target has been known (for example, see International Patent Publications WO/2013/145407 and WO/2013/145409).

SUMMARY

The present disclosure is directed to an image processing apparatus, an endoscope system, an image processing apparatus operating method, and a computer readable recording medium.

According to an aspect of the present disclosure, an endoscope system is provided which includes a light source operable to irradiate a first narrowband light and a second narrowband light to a subject to be examined, the first and second narrowband light being included in an observation target wavelength band ranging from a wavelength at which an absorption coefficient takes a local maximum value to a wavelength at which the absorption coefficient takes a local minimum value in a hemoglobin absorption characteristic of a living tissue, wherein the second narrowband light yields a lower absorption coefficient and a lower scattering coefficient by a living tissue than the first narrowband light; an imaging sensor operable to capture an image of return light of the first narrowband light and the second narrowband light from the subject, and to generate an image signal of the image; and a processor comprising hardware, wherein the processor is configured to identify a first color of a first portion and a second color of a second portion in accordance with a difference of an optical density with respect to hemoglobin in the image signal in every frame of the image captured by the image sensor, the first portion corresponding to a bleeding area within the subject, and the second portion corresponding to an area other than the bleeding area within the subject, and correct the first color and the second color in accordance with the identified first color and the identified second color while maintaining a color difference between the identified first color and the identified second color in a predetermined range.

The above and other features, advantages and technical and industrial significance of this disclosure will be better understood by reading the following detailed description of presently preferred embodiments of the disclosure, when considered in connection with the accompanying drawings.

DETAILED DESCRIPTION

Exemplary embodiments of an image processing apparatus, an image processing apparatus operating method, and a computer readable recording medium according to the present disclosure will be described below with reference to the drawings. The present disclosure is not limited by the embodiments below. In the embodiments below, an endoscope system including an image processing apparatus will be described by way of example; however, the present disclosure may be applied to general image capturing systems including image processing apparatuses.

Further, in descriptions of the drawings, the same or corresponding components are appropriately denoted by the same reference signs. Furthermore, it is necessary to note that the drawings are schematic, and dimensional relations of each of components, ratios among components, and the like may be different from actual ones. Moreover, the drawings may include a portion that has different dimensional relations or ratios.

First Embodiment

Configuration of Endoscope System

Figure 1:
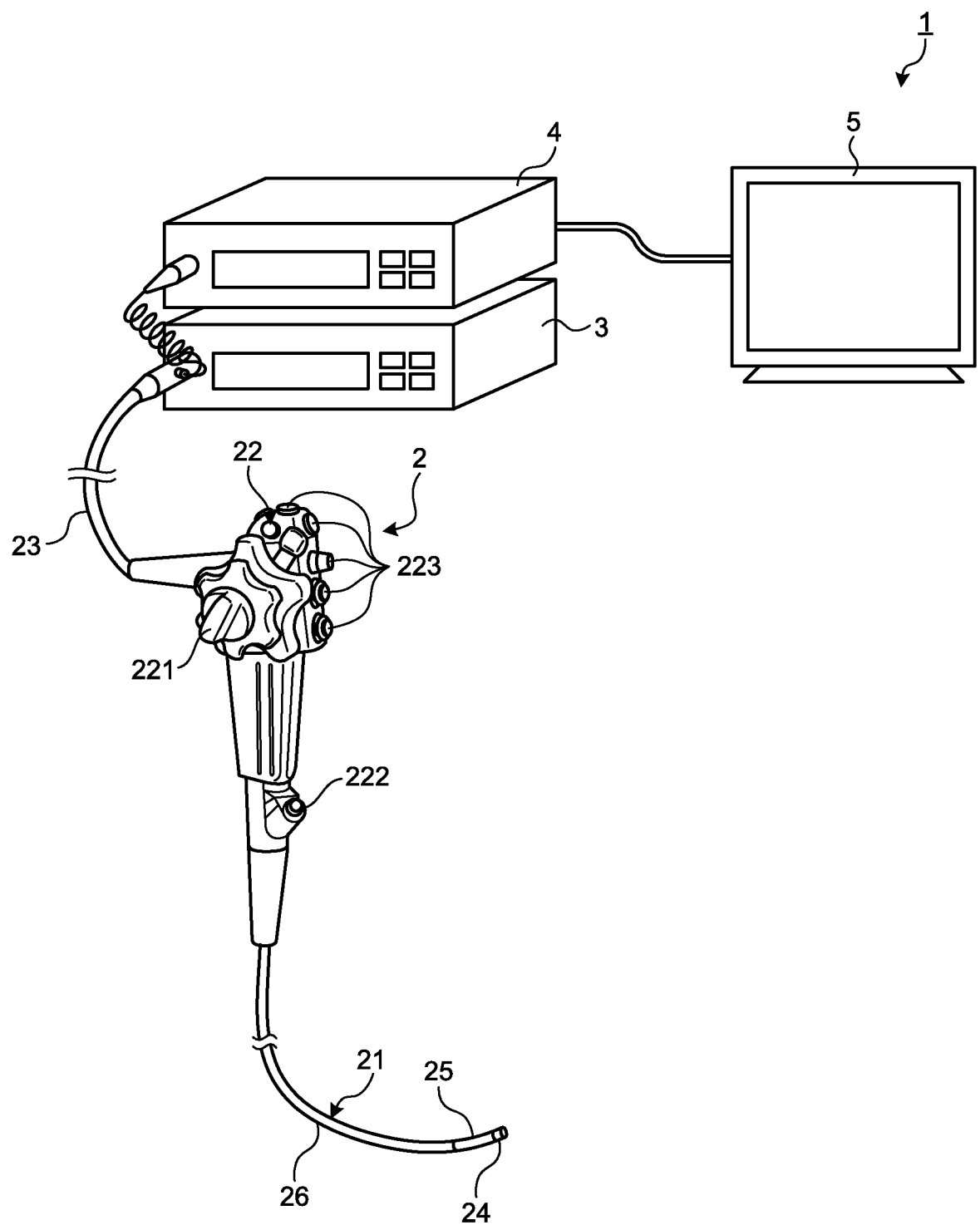
FIG. 1 is a diagram illustrating a schematic configuration of an endoscope system including an image processing apparatus according to a first embodiment of the present disclosure.
Figure 2:
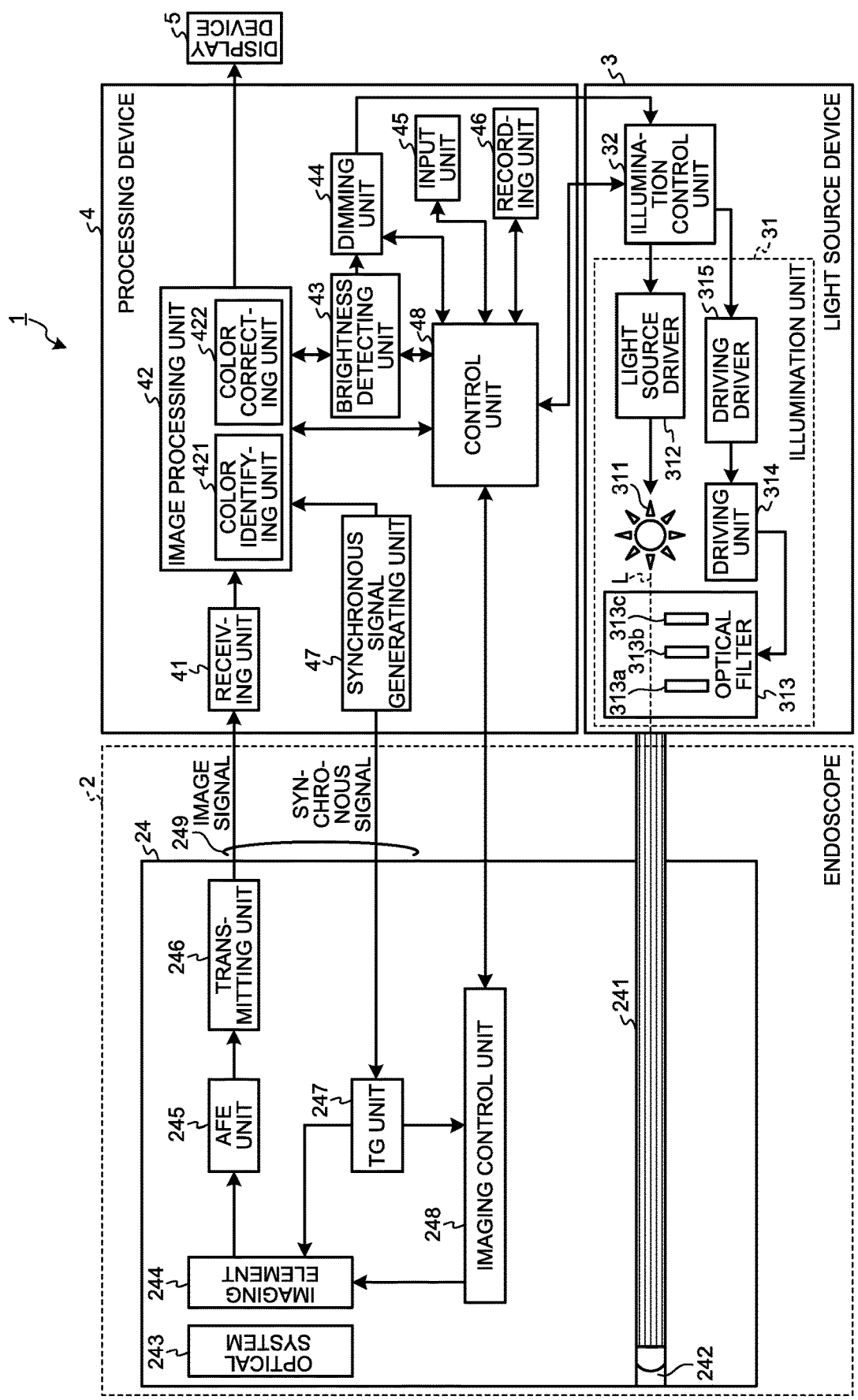
FIG. 2 is a block diagram illustrating a functional configuration of main components of the endoscope system including the image processing apparatus according to the first embodiment of the present disclosure.

FIG. 1 is a diagram illustrating a schematic configuration of an endoscope system including an image processing apparatus according to a first embodiment of the present disclosure. FIG. 2 is a block diagram illustrating a functional configuration of main components of the endoscope system including the image processing apparatus according to the first embodiment of the present disclosure.

An endoscope system 1 illustrated in FIG. 1 and FIG. 2 includes: an endoscope 2 (endoscopic scope) serving as an image capturing unit that captures an image signal of a subject by inserting a distal end portion thereof into a body cavity of the subject; a light source device 3 serving as a light source unit that generates illumination light to be emitted from a distal end of the endoscope 2; a processing device 4 serving as an image processing apparatus that performs predetermined image processing on the image signal captured by the endoscope 2 and comprehensively controls entire operation of the endoscope system 1; and a display device 5 that displays an observation image (in-vivo image) corresponding to the image signal that is subjected to the image processing by the processing device 4. In the first embodiment, an example will be described in which the endoscope 2 is a flexible endoscope, but it may be possible to adopt any of a three-dimensional (3D) endoscope, a rigid endoscope, and a nasal endoscope.

Configuration of Endoscope

First, a configuration of the endoscope 2 will be described.

The endoscope 2 includes a flexible elongated insertion portion 21, an operating unit 22 that is connected to a proximal end side of the insertion portion 21 and receives input of various operation signals, and a universal cord 23 that extends from the operating unit 22 in a direction different from a direction along which the insertion portion 21 extends and that has various built-in cables connected to the light source device 3 and the processing device 4.

The insertion portion 21 includes a distal end portion 24 that has a built-in imaging element 244 in which pixels that receive light and perform photoelectric conversion to generate an electrical signal (image signal) are two-dimensionally arranged, a bending portion 25 that is constructed by a plurality of bending pieces and is freely bendable, and an elongated flexible tube portion 26 that is connected to a proximal end side of the bending portion 25 and has flexibility.

Referring to FIG. 2, the distal end portion 24 includes a light guide 241, an illumination lens 242, an optical system 243, the imaging element 244, an analog front end unit 245 (hereinafter, referred to as the "AFE unit 245"), a transmitting unit 246, a timing generator unit 247 (hereinafter, referred to as the "TG unit 247"), and an imaging control unit 248.

The light guide 241 (FIG. 1) is constructed with an optical fiber or the like, and serves as a light-guiding path for light emitted by the light source device 3. The illumination lens 242 is disposed on a distal end of the light guide 241 and irradiates the light, which has been guided by the light guide 241, to an object.

The optical system 243 is constructed with one or a plurality of lenses, a prism, and the like, and has an optical zoom function to change an angle of view and a focus function to change a focal point.

The imaging element 244 performs photoelectric conversion on the light received from the optical system 243 and generates an electrical signal as an image signal. The imaging element 244 is constructed with an image sensor, such as a charge coupled device (CCD) or a complementary metal oxide semiconductor (CMOS). The imaging element 244 is disposed on an image focusing plane onto which the optical system 243 focuses an object image. The imaging element 244 generates an image signal in accordance with a signal input from the TG unit 247 under the control of the imaging control unit 248.

The AFE unit 245 reduces a noise component that is included in the image signal input from the imaging element 244, performs a correlated double sampling (CDS) process for adjusting an amplification factor of the image signal to maintain a constant output level, an analog-to-digital (A/D) conversion process for performing A/D conversion on the image signal, and the like, and then outputs the image signal to the transmitting unit 246.

The transmitting unit 246 transmits the digital image signal input from the AFE unit 245 to the processing device 4. The transmitting unit 246 performs, for example, a parallel-to-serial conversion process for converting a parallel image signal to a serial image signal or an electrical-to-optical conversion process for converting an electrical image signal to an optical image signal, and transmits the converted image signal to the processing device 4.

The TG unit 247 generates pulse signals for various kinds of signal processing to drive each of the imaging element 244 and the imaging control unit 248. The TG unit 247 outputs pulse signals to the imaging element 244 and the imaging control unit 248.

The imaging control unit 248 controls imaging performed by the imaging element 244. The imaging control unit 248 is constructed with a central processing unit (CPU), a register for recording various programs, and the like.

The operating unit 22 includes a bending knob 221 for bending the bending portion 25 in a vertical direction and a horizontal direction; a treatment tool insertion portion 222 for inserting a treatment tool, such as a biopsy forceps, an electric scalpel, and an inspection probe, into a body cavity of the subject; and a plurality of switches 223 serving as an operation input unit for inputting an operation instruction signal to the light source device 3, the processing device 4, the display device 5, and peripheral devices, such as an air supply means and a water supply means. The treatment tool inserted from the treatment tool insertion portion 222 gets out of an opening (not illustrated) via a treatment tool channel (not illustrated) of the distal end portion 24.

The universal cord 23 has at least the built-in light guide 241, and a built-in assembly cable 249 into which one or more signal lines are bundled. The assembly cable 249 includes at least a signal line for transmitting a synchronous signal output from the processing device 4 (to be described later) and a signal line for transmitting the image signal.

Configuration of Light Source Device

Next, a configuration of the light source device 3 will be described.

The light source device 3 includes an illumination unit 31 and an illumination control unit 32.

The illumination unit 31 is configured to emit plural kinds of illumination light in different wavelength bands, and emits any one of the plural kinds of illumination light to an object (subject) as appropriate under the control of the illumination control unit 32. The illumination unit 31 includes a light source unit 311, a light source driver 312, an optical filter 313, a driving unit 314, and a driving driver 315.

The light source unit 311 is constructed with a white light emitting diode (LED), one or more lenses, and the like, and emits white light to the optical filter 313 under the control of the light source driver 312. The white light generated by the light source unit 311 is emitted toward the object from a distal end of the distal end portion 24 via the optical filter 313 and the light guide 241. Meanwhile, the light source unit 311 may be constructed with a red LED, a green LED, and a blue LED, and emits red light, green light, or blue light as appropriate when the light source driver 312 supplies an electric current to each of the LEDs. Further, the light source unit 311 may be constructed with from a white LED, a red LED, a green LED, and a blue LED, and emit white light, red light, green light, or blue light as appropriate. Additionally, the light source unit 311 may be constructed with a discharge lamp, such as a xenon lamp, and emits white light to the subject, of which image is then captured by the imaging element 244.

The light source driver 312 supplies an electric current to the light source unit 311 to cause the light source unit 311 to emit white light under the control of the illumination control unit 32.

The optical filter 313 is constructed with a plurality of filters that transmit light only in a predetermined wavelength band. The optical filter 313 is disposed such that a predetermined filter is removably inserted into an optical path L (FIG. 1) of the white light emitted by the light source unit 311 under the control of the driving unit 314. The optical filter 313 has a transmission characteristic that limits a wavelength band of the while light emitted from the light source unit 311 to a predetermined wavelength band. The optical filter 313 is disposed by the driving unit 314 so as to be removably inserted into the optical path L of the white light emitted by the light source unit 311.

A filter 313a transmits red (R) light, green (G) light, or blue (B) light in respective wavelength bands (for example, red: wavelengths of 600 nm to 700 nm, green: wavelengths of 500 nm to 600 nm, and blue: wavelengths of 400 nm to 500 nm). When the endoscope system 1 performs white light imaging (WLI), the filter 313a is inserted into the optical path L of the white light and rotated by the driving unit 314, so that red light (R illumination), green light (G illumination), and blue light (B illumination) in narrow bands are sequentially input into the endoscope 2 and an image of the subject is captured according to a frame sequential method.

A filter 313b transmits blue light in a narrow band (for example, wavelengths of 390 nm to 445 nm) and green light in a narrow band (for example, wavelengths of 530 nm to 550 nm). Specifically, when the endoscope system 1 performs narrow band imaging (NBI) as special light imaging, the filter 313b is inserted into the optical path L of the white light by the driving unit 314.

A filter 313c transmits a first red narrowband light (for example, a wavelength of 600 nm and around) and a second red narrowband light (for example, a wavelength of 630 nm and around). The first red narrowband light is included in an observation target wavelength band ranging from a wavelength at which an absorption coefficient takes a local maximum value to a wavelength at which the absorption coefficient takes a local minimum value in a hemoglobin absorption characteristic. The second red narrowband light is also included in the above-described observation target wavelength band. However, an absorption coefficient of the second red narrowband light is lower than that of the first red narrowband light; and a scattering coefficient by a living tissue under the second red narrowband light is lower than that of the first red narrowband light. In other words, light that has transmitted through the filter 313c has a narrowband spectral characteristic. When the endoscope system 1 performs dual red imaging (DRI) as special light imaging, the filter 313c is inserted into the optical path L of the white light by the driving unit 314. In DRI, it is possible to emphasize a bleeding point, a blood vessel, and the like that have large optical densities with respect to hemoglobin.

Meanwhile, the optical filter 313 may include a filter that transmits excitation light (for example, wavelengths of 390 nm to 470 nm). The excitation light may be used when the endoscope system 1 performs fluorescence observation (auto fluorescence imaging (AFI)) as special light imaging, wherein auto fluorescence that occurs from a fluorescent material, such as collagen is observed. Additionally, the filter 313 may include a filter that transmits light having wavelengths (for example, wavelengths of 540 nm to 560 nm) that can be absorbed by hemoglobin in blood. Moreover, the filter 313 may include a filter that transmits two kinds of infrared light (for example, light of wavelengths from 790 nm to 820 nm and light of wavelengths from 905 nm to 970 nm) when the endoscope system 1 performs infrared imaging (IRI) as special light imaging.

The driving unit 314 is constructed with a stepping motor, a DC motor, or the like, and arranges each of the filters included in the optical filter 313 into the optical path L of the white light under the control of the driving driver 315.

The driving driver 315 supplies a predetermined electric current to the driving unit 314 under the control of the illumination control unit 32.

The illumination control unit 32 causes the light source unit 311 to emit white light with a predetermined period, on the basis of an instruction signal input from the processing device 4.

Configuration of Processing Device

Next, a configuration of the processing device 4 will be described.

The processing device 4 includes a receiving unit 41, an image processing unit 42, a brightness detecting unit 43, a dimming unit 44, an input unit 45, a recording unit 46, a synchronous signal generating unit 47, and a control unit 48.

The receiving unit 41 receives an image signal transmitted from the transmitting unit 246 and outputs the image signal to the image processing unit 42. When the image signal transmitted from the transmitting unit 246 is a parallel signal, the receiving unit 41 performs a parallel-to-serial conversion process for converting the parallel signal into a serial signal and outputs the converted image signal to the image processing unit 42. When the image signal transmitted from the transmitting unit 246 is an optical signal, the receiving unit 41 performs an optical-to-electrical (O/E) conversion process for converting the optical signal into an electrical signal and outputs the converted image signal to the image processing unit 42.

The image processing unit 42 is constructed with a field programmable gate array (FPGA) or the like. The image processing unit 42 performs image processing on the image signal that is captured by the imaging element 244 and input via the receiving unit 41 or the like, generates an in-vivo image to be displayed by the display device 5, and outputs the in-vivo image to the display device 5, under the control of the control unit 48. The image processing unit 42 generates the in-vivo image by performing predetermined image processing on the image signal. Here, examples of the image processing include a synchronization process, an optical black reduction process, a white balance adjustment process, a color matrix calculation process, a gamma correction process, a color reproduction process, an edge enhancement process, and a format conversion process. The image processing unit 42 includes a color identifying unit 421 and a color correcting unit 422.

Figure 3:
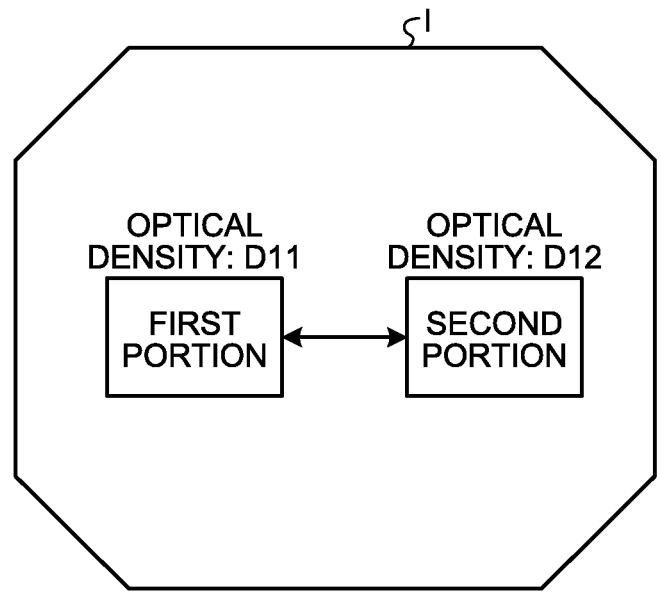
FIG. 3 is a diagram illustrating a first portion and a second portion that are set in an endoscopic image.

The color identifying unit 421 identifies color tones of at least a first portion and a second portion of an image signal. FIG. 3 is a diagram illustrating the first portion and the second portion that are set in an endoscopic image. As illustrated in FIG. 3, the first portion and the second portion are set in an endoscopic image I (image signal). The first portion and the second portion are portions that respectively have an optical density D11 and an optical density D12 as optical densities with respect to hemoglobin in a living tissue. The optical density D11 of the first portion is larger than the optical density D12 of the second portion. For example, the first portion with the larger optical density than the second portion corresponds to a bleeding point of a living tissue, and the second portion corresponds to a portion other than the bleeding point. The first portion and the second portion may be manually set by a user who observes the endoscopic image I or may be automatically set with respect to regions that include pixels of predetermined colors by predetermined image processing or by using values or the like detected by a sensor. Further, the first portion and the second portion may be set at the start of observation, or may be set every time the imaging element 244 captures an image (for each frame).

Figure 4:
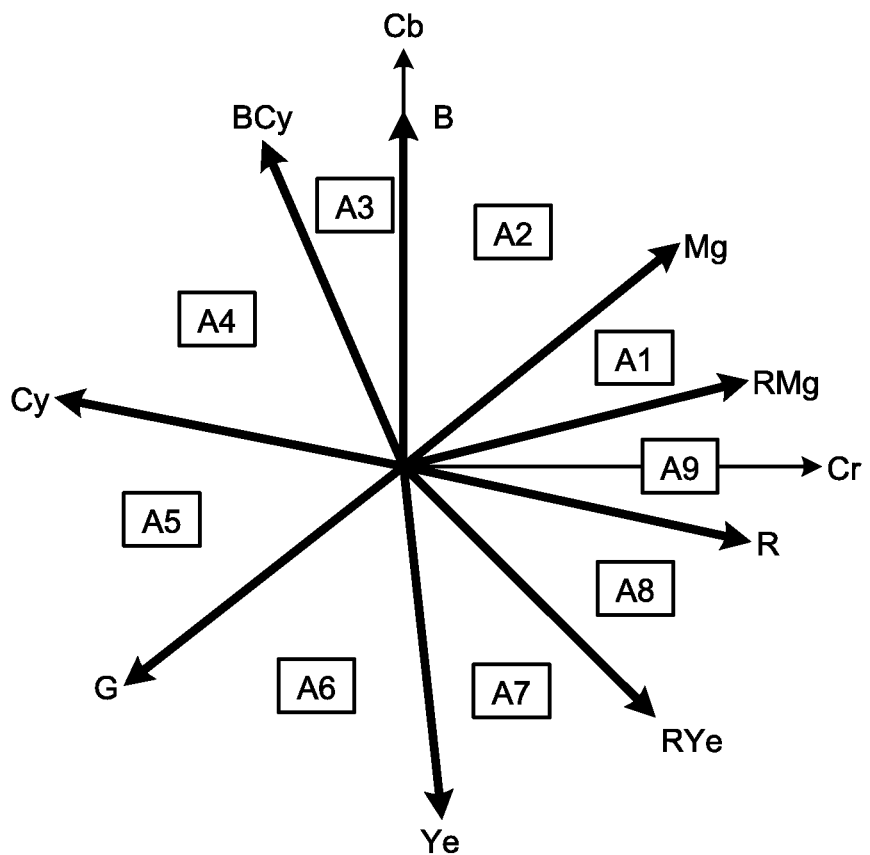
FIG. 4 is a diagram illustrating a color space that is defined by nine reference axes that are set for a plurality of hues.
Figure 5:
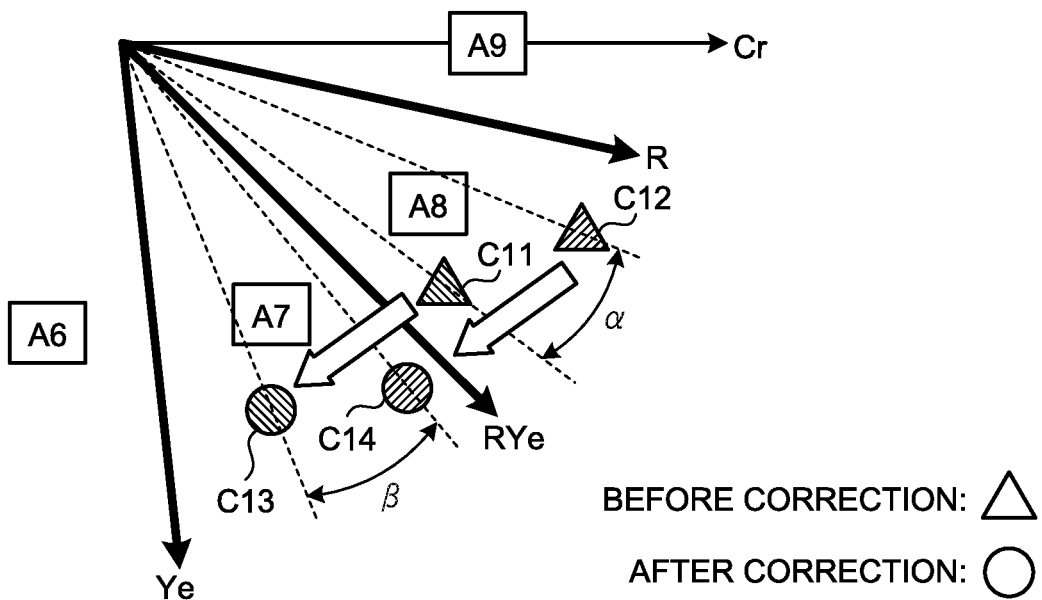
FIG. 5 is a diagram illustrating colors of the first portion and the second portion in the color space before and after correction.

The color identifying unit 421 identifies colors of the first portion and the second portion by matching the colors with respective points on a color space. FIG. 4 is a diagram illustrating a color space that is defined by nine reference axes that are set for a plurality of hues. As illustrated in FIG. 4, for example, the color space is defined by nine reference axes that are set for hues of magenta (Mg), blue (B), blue cyan (BCy), cyan (Cy), green (G), yellow (Ye), red yellow (RYe), red (R), and red magenta (RMg). In the color space, a color is identified by a hue that is represented by an angle with respect to the reference axes and saturation that is represented by a distance from a center. FIG. 5 is a diagram illustrating the colors of the first portion and the second portion in the color space before and after correction. As illustrated in FIG. 5, the color identifying unit 421 identifies a point C11 and a point C12 in the color space as the respective colors of the first portion and the second portion. Meanwhile, the color of each of the first portion and the second portion is an average value of colors of pixels included in the first portion or the second portion, but may be a statistical value, such as a mode value, an intermediate value, a maximum value, or a minimum value, of the colors of the pixels included in the first portion or the second portion.

The color correcting unit 422 corrects the colors of the first portion and the second portion while maintaining a color difference between the color of the first portion and the color of the second portion in a predetermined range, on the basis of the color of the first portion and the color of the second portion identified by the color identifying unit 421. Specifically, the color correcting unit 422 performs a color matrix calculation process and a nine-axis color gamut adjustment process.

First, the image signal (the endoscopic image I) captured by the imaging element 244 is a color signal including an R signal, a G signal, and a B signal. The color correcting unit 422 multiplies an input signal ($R_{in}$, $G_{in}$, $B_{in}$) by a matrix coefficient Mat[0][0] to Mat[2][2] to calculate an output signal ($R_{out}$, $G_{out}$, $B_{out}$) based on Equation (1) below.

$$\begin{pmatrix} R_{out} \\ G_{out} \\ B_{out} \end{pmatrix} = \begin{pmatrix} (Mat[0][0]) & (Mat[0][1]) & (Mat[0][2]) \\ (Mat[1][0]) & (Mat[1][1]) & (Mat[1][2]) \\ (Mat[2][0]) & (Mat[2][1]) & (Mat[2][2]) \end{pmatrix} \begin{pmatrix} R_{in} \\ G_{in} \\ B_{in} \end{pmatrix} \quad (1)$$

Further, the color correcting unit 422 converts the output signal that is a color signal including an R signal, a G signal, and a B signal into a Y signal, a Cr signal, and a Cb signal. Then, the converted signal is determined to be positioned in which one of the nine hue regions (A1 to A9 in FIG. 4) by comparing magnitudes of the Cr signal and the Cb signal.

To perform a color correction process on each of the nine hue regions, the recording unit 46 stores therein, in advance, processing conditions including nine saturation (color saturation) correction coefficients of $KR_{sat}$, $KG_{sat}$, $KB_{sat}$, $KY_{esat}$, $KC_{ysat}$, $KM_{gsat}$, $KRY_{esat}$, $KRM_{gsat}$, $KBC_{ysat}$ and nine hue correction coefficients of $KR_{hue}$, $KG_{hue}$, $KB_{hue}$, $KY_{ehue}$, $KC_{yhue}$, $KM_{ghue}$, $KRY_{ehue}$, $KRM_{ghue}$, $KBC_{yhue}$. Here, letters following a symbol "K" that represents a correction coefficient is an abbreviation of a hue, where RMg represents an intermediate color between R and Mg, RYe represents an intermediate color between R and Ye, and BCy represents an intermediate color between B and Cy.

The control unit 48 outputs four correction coefficients of $K_{sat1}$, $K_{sat2}$, $K_{hue1}$, $K_{hue2}$, which are processing conditions related to the hue region in which a color signal of a pixel of the endoscopic image I is located, to the color correcting unit 422 on the basis of setting values of the processing conditions and the magnitude relationship between the Cr signal and the Cb signal. Meanwhile, the color correcting unit 422 calculates vector quantities $d_p$ and $d_c$, which are vector quantities along color axes defining the hue region in which the points corresponding to the colors of the first portion and the second portion of the endoscopic image I are located. The color correcting unit 422 calculates correction coefficients based on Equations (2) and (3) below, using the processing conditions received from the control unit 48 and the calculated vector quantities.

$$Cr_{out} = Cr_{in} + p_{sat}(p_{hue} \times Cr_{-a1}) + c_{sat}(c_{hue} \times Cr_{a2}) \quad (2)$$

$$Cb_{out} = Cb_{in} + p_{sat}(p_{hue} \times Cb_{-a1}) + c_{sat}(c_{hue} \times Cb_{a2}) \quad (3)$$

The color correcting unit 422 performs the color correction process on the endoscopic image I based on Equations (4) to (7) below, using fixed correction coefficients of $Cr_{-a1}$, $Cb_{-a1}$, $Cr_{-a2}$, $Cb_{-a2}$ and calculated correction coefficients of $p_{sat}$, $p_{hue}$, $c_{sat}$, $c_{hue}$.

$$p_{sat} = K_{sat1} \times d_p \quad (4)$$

$$p_{hue} = K_{hue1} \times d_p \quad (5)$$

$$c_{sat} = K_{sat2} \times d_c \quad (6)$$

$$c_{hue} = K_{hue2} \times d_c \quad (7)$$

When the color correcting unit 422 performs correction as described above, as illustrated in FIG. 5, the point corresponding to the color of the first portion is corrected from the point C11 to a point C13, and the point corresponding to the color of the second portion is corrected from the point C12 to a point C14. In this case, the color correcting unit 422 performs correction such that an angle α between the first portion and the second portion before the correction and an angle β between the first portion and the second portion after the correction become approximately equal to each other.

The brightness detecting unit 43 detects a brightness level corresponding to each image on the basis of RGB image information that is included in the image signal input from the image processing unit 42, records the detected brightness level in an internal memory, and outputs the brightness level to each of the dimming unit 44 and the control unit 48.

The dimming unit 44 sets a light emitting condition, such as a light quantity or a light emitting timing, on light emitted by the light source device 3 on the basis of the brightness level detected by the brightness detecting unit 43 and outputs a dimming signal including the set light emitting condition to the light source device 3, under the control of the control unit 48.

The input unit 45 receives input of various signals, such as an operation instruction signal for giving an instruction on operation of the endoscope system 1. The input unit 45 is constructed with a switch or the like. The input unit 45 receives input of an instruction signal for changing any one of setting values of a plurality of modes and a plurality of kinds of image processing.

The recording unit 46 is realized by using a read only memory (ROM), and stores therein various programs for operating the endoscope system 1, data including various parameters that are necessary for operation of the endoscope system 1, and the like.

The synchronous signal generating unit 47 generates a synchronous signal including at least a vertical synchronous signal, outputs the synchronous signal to the TG unit 247 via the assembly cable 249, and outputs the synchronous signal to the image processing unit 42.

The control unit 48 is constructed with a CPU or the like, and controls drive of each of the components including the imaging element 244 and the light source device 3, input and output of information to and from each of the components, and the like.

As described above, according to the first embodiment, the color correcting unit 422 performs correction such that the angle α and the angle β that represent hue differences between the first portion and the second portion before and after hue correction become approximately equal to each other. Here, the color difference is defined as a distance between the color of the first portion and the color of the second portion in the color space. Therefore, as illustrated in FIG. 5, when the color correcting unit 422 performs correction such that the angle α, which represents the hue difference between the first portion and the second portion before the correction, and the angle β, which represents the hue difference between the first portion and the second portion after the correction, become approximately equal to each other, and such that a saturation difference between the first portion and the second portion before the correction and a saturation difference between the first portion and the second portion after the correction become approximately equal to each other, a distance between the point C11 and the point C12 and a distance between the point C13 and the point C14 become approximately equal to each other; therefore, it is possible to correct the colors while maintaining the color difference. However, although it is possible to improve visibility while maintaining the hue difference and the saturation difference before and after the correction by approximately equalizing both of the hue difference and the saturation difference between the first portion and the second portion before and after the correction, it is not always necessary to approximately equalize both of the hue difference and the saturation difference as long as the color difference is maintained before and after the correction.

If a color tone of an entire endoscopic image is corrected from red to yellow through image processing, in some cases, an effect to improve visibility of a bleeding point may be reduced. However, according to the first embodiment, because the color difference between the first portion representing a bleeding point and the second portion representing a portion other than the bleeding point is maintained, it is possible to maintain the effect to improve visibility of a bleeding point by DRI even when the processing device 4 performs image processing.

Second Embodiment

An image processing apparatus according to a second embodiment is different from the first embodiment in that the image processing apparatus performs a different process. Other configurations of the second embodiment are the same as those of the first embodiment illustrated in FIG. 1, and therefore, explanation thereof will be appropriately omitted.

Figure 6:
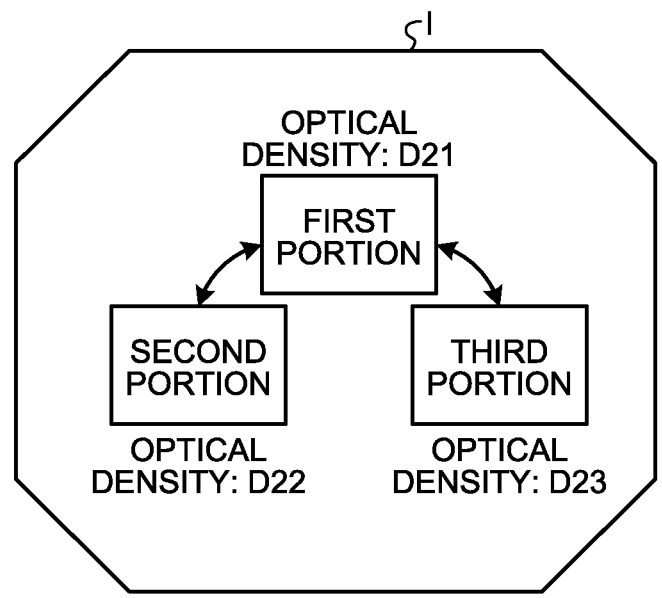
FIG. 6 is a diagram illustrating a first portion, a second portion, and a third portion that are set in the endoscopic image.

The color identifying unit 421 identifies colors of a first portion, a second portion, and a third portion in the image signal. FIG. 6 is a diagram illustrating the first portion, the second portion, and the third portion that are set in the endoscopic image. As illustrated in FIG. 6, the first portion, the second portion, and the third portion are set in the endoscopic image I (image signal). The first portion, the second portion, and the third portion are portions that respectively have an optical density D21, an optical density D22, and an optical density D23 as optical densities with respect to hemoglobin in a living tissue. It is assumed that a magnitude relationship of these optical densities is that the optical density D21<the optical density D22<the optical density D23. The first portion, the second portion, and the third portion may be manually set by a user who observes the endoscopic image I or may be automatically set to regions that include pixels of predetermined colors by predetermined image processing.

Figures 7, 8:
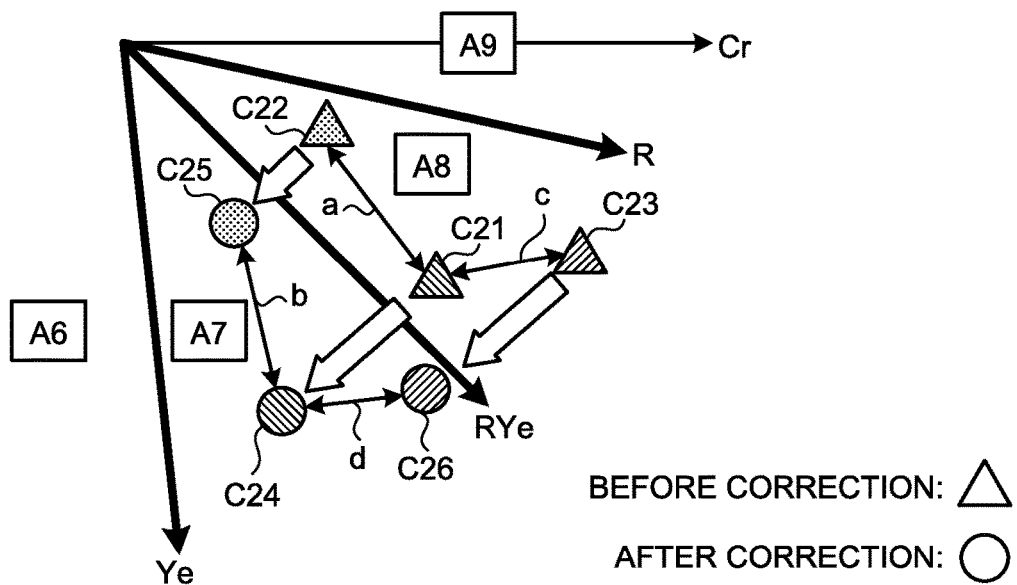
FIG. 7 is a diagram illustrating colors of the first portion, the second portion, and the third portion in the color space before and after correction.
FIG. 8 is a diagram illustrating a first portion to a fourth portion.

The color identifying unit 421 identifies colors of the first portion, the second portion, and the third portion by matching the colors with respective points in the color space. FIG. 7 is a diagram illustrating the colors of the first portion, the second portion, and the third portion in the color space before and after correction. As illustrated in FIG. 7, the color identifying unit 421 identifies a point C21, a point C22, and a point C23 in the color space as the respective colors of the first portion, the second portion, and the third portion.

The color correcting unit 422 corrects the colors of the first portion, the second portion, and the third portion while maintaining a color difference between the color of the first portion and the color of the second portion and a color difference between the color of the first portion and the color of the third portion in predetermined ranges. Specifically, the color correcting unit 422 performs the color matrix calculation process and the nine-axis color gamut adjustment process as described above, and corrects the points corresponding to the colors of the first portion, the second portion, and the third portion from the point C21, the point C22, and the point C23 to a point C24, a point C25, and a point C26, respectively, as illustrated in FIG. 7. In this case, the color correcting unit 422 corrects hues and saturation such that a distance a and a distance b between the first portion and the second portion in the color space before and after the correction become approximately equal to each other and such that a distance c and a distance d between the first portion and the third portion in the color space before and after the correction become approximately equal to each other.

As in the second embodiment as described above, it may be possible to perform image processing while maintaining color differences among three portions in the endoscopic image I.

Third Embodiment

An image processing apparatus according to a third embodiment is different from the first embodiment in that the image processing apparatus performs a different process. Other configurations of the third embodiment are the same as those of the first embodiment illustrated in FIG. 1, and therefore, explanation thereof will be appropriately omitted.

The color identifying unit 421 identifies colors of a first portion, a second portion, a third portion, and a fourth portion in the image signal. FIG. 8 is a diagram illustrating the first portion to the fourth portion. As illustrated in FIG.

8, the first portion represents a portion in which arterial bleeding occurs or a portion which is attenuated by saline. The second portion represents a portion in which venous bleeding occurs or a portion which is attenuated by saline. The third portion represents an arterial bleeding point. The fourth portion represents a venous bleeding point.

Figure 9:
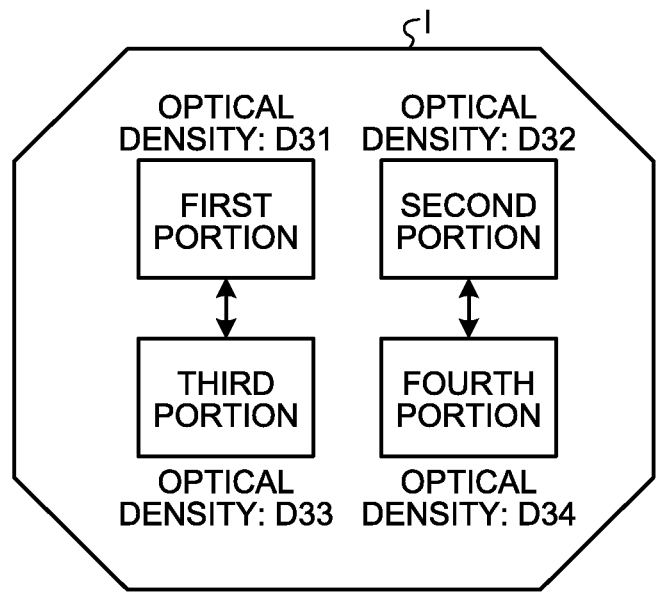
FIG. 9 is a diagram illustrating the first portion to the fourth portion that are set in the endoscopic image.

FIG. 9 is a diagram illustrating the first portion to the fourth portion that are set in the endoscopic image. The first portion to the fourth portion are set in the endoscopic image I (image signal). The first portion to the fourth portion are portions that respectively have an optical density D31, an optical density D32, an optical density D33, and an optical density D34 as optical densities with respect to hemoglobin in a living tissue. The first portion to the fourth portion may be manually set by a user who observes the endoscopic image I or may be automatically set to regions that include pixels of predetermined colors by predetermined image processing.

The color identifying unit 421 identifies colors of the first portion to the fourth portion by matching the colors with respective points in the color space. Further, the color correcting unit 422 corrects the colors of the first portion to the fourth portion while maintaining a color difference between the color of the first portion and the color of the third portion and a color difference between the color of the second portion and the color of the fourth portion in predetermined ranges. Meanwhile, it is possible to adopt the same color identification method and the same color correction method as those of the first embodiment, and therefore, explanation of the methods will be omitted.

As described above, according to the third embodiment, by maintaining the color difference between the color of the first portion and the color of the third portion and the color difference between the color of the second portion and the color of the fourth portion in predetermined ranges, it is possible to maintain visibility of a bleeding point in each of arterial blood and venous blood.

Modification of Third Embodiment

Figure 10:
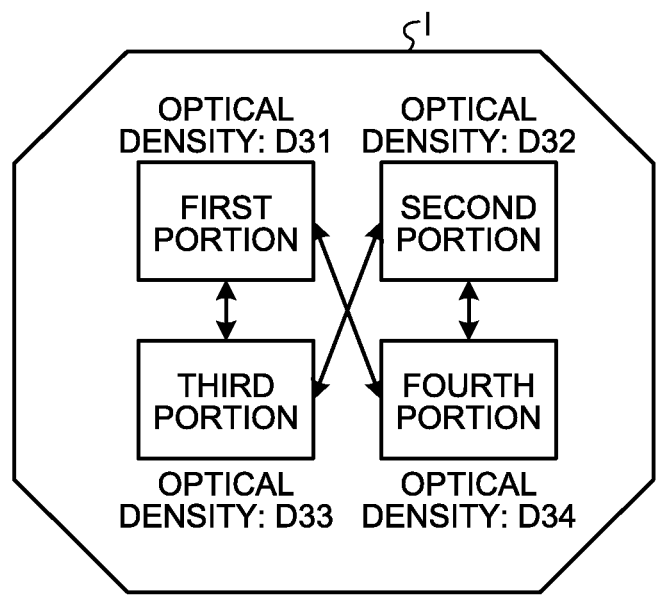
FIG. 10 is a diagram illustrating the first portion to the fourth portion that are set in the endoscopic image.

FIG. 10 is a diagram illustrating a first portion to a fourth portion that are set in the endoscopic image. As illustrated in FIG. 10, in a modification of the third embodiment, the color correcting unit 422 corrects colors of the first portion to the fourth portion while maintaining a color difference between the color of the first portion and the color of the third portion, a color difference between the color of the second portion and the color of the fourth portion, a color difference between the color of the first portion and the color of the fourth portion, and a color difference between the color of the second portion and the color of the third portion in predetermined ranges. As a result, according to the modification of the third embodiment, even when arterial blood and venous blood are mixed, it is possible to maintain visibility of a bleeding point.

Meanwhile, while an example has been described in which colors are corrected while maintaining a color difference between a plurality of portions in the endoscopic image I in the embodiments described above, embodiments are not limited to this example. The color correcting unit 422 may correct a color tone of an entire endoscopic image such that a color corresponding to a predetermined region including a red region in the color space to a yellow region in the color space. More specifically, the color correcting unit 422 may perform correction such that a color corresponding to a region from G to Mg including Rye in the color space approaches Ye in the color space. Similarly, the color correcting unit 422 may perform correction such that a color corresponding to a region from Ye to R including Rye in the color space approaches Ye in the color space.

Furthermore, while an example has been described in which the color correcting unit 422 performs both of the color matrix calculation process and the nine-axis color gamut adjustment process in the embodiments described above, embodiments are not limited to this example. The color correcting unit 422 may be configured to perform only one of the color matrix calculation process and the nine-axis color gamut adjustment process.

Moreover, while the color space defined by the nine reference axes is used in the embodiments described above, the number of reference axes and the way of defining the color space are not specifically limited.

Furthermore, while the configuration in which the processing device 4 includes the color identifying unit 421 is illustrated in the embodiments described above, the color identifying unit may be included in the endoscope.

Moreover, while the configuration in which the processing device 4 includes the color identifying unit 421 and the color correcting unit 422 is illustrated in the embodiments described above, embodiments are not limited to this configuration. For example, the processing device 4 may be configured so as to be able to add functions corresponding to the color identifying unit 421 and the color correcting unit 422 via the Internet (cloud or software downloading).

Furthermore, while the image signal is transmitted to the processing device 4 via a transmission cable in the embodiments described above, the transmission need not always be performed in a wired manner, but may be performed in a wireless manner. In this case, it is sufficient to transmit the image signal and the like to the processing device 4 in accordance with a predetermined wireless communication standard (for example, Wi-Fi (registered trademark) or Bluetooth (registered trademark)). It is of course possible to perform wireless communication in accordance with other wireless communication standards.

Moreover, while the processing device 4 and the light source device 3 are configured as separate bodies in the embodiments described above, embodiments are not limited to this example. For example, the processing device and the light source device may be integrated with each other.

Furthermore, while the endoscope of the frame sequential method is illustrated as an example in the embodiments described above, it may be possible to adopt an endoscope of a simultaneous method.

Moreover, while the endoscope 2 to be inserted into a subject is adopted in the embodiments described above, it may be possible to adopt, for example, a capsule endoscope or an imaging apparatus that captures an image of a subject.

According to the present disclosure, it is possible to realize an image processing apparatus, an image processing apparatus operation method, and a computer readable recording medium capable of maintaining an effect to improve visibility of an observation target regardless of imaging conditions.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. An endoscope processor comprising:
a light source configured to irradiate a first narrowband light and a second narrowband light to a subject to be examined, the first and second narrowband light being included in an observation target wavelength band ranging from a wavelength at which an absorption coefficient takes a local maximum value to a wavelength at which the absorption coefficient takes a local minimum value in a hemoglobin absorption characteristic of a living tissue, wherein the second narrowband light yields a lower absorption coefficient and a lower scattering coefficient by a living tissue than the first narrowband light; and
a processor configured to be connected to an endoscope, the endoscope being configured to capture an image of return light of the first narrowband light and the second narrowband light from the subject, and to generate an image signal of the image,
wherein the processor is configured to:
  generate a first image in which the bleeding area is emphasized, from the image signal; and
  perform a second image generation processing of generating a second image, the second image generation processing comprising:
    identify a first color of a first portion of the first image and a second color of a second portion of the first image by associating the first color with a first point in a color space and the second color with a second point in the color space, the first color corresponding to the bleeding area within the subject, the second color corresponding to an area other than the bleeding area within the subject;
    correct the first color such that the first point associated with the first color is corrected to a third point associated with a color in the color space between hues of yellow and red-yellow; and
    correct the second color such that the second point associated with the second color is corrected to a fourth point in the color space, wherein a first distance between the first point and the second point in the color space is substantially equal to a second distance between the third point and the fourth point.

2. The endoscope processor according to claim 1, wherein the color space is defined by nine reference axes that are set for a plurality of hues of magenta (Mg), blue (B), blue cyan (BCy), cyan (Cy), green (G), yellow (Ye), red yellow (RYe), red (R), and red magenta (RMg), and
wherein the processor is further configured to perform correction such that a color corresponding to a region from green to magenta including red yellow in the color space approaches yellow in the color space.

3. The endoscope processor according to claim 2, wherein the processor is further configured to perform correction such that a color corresponding to a region from yellow to red including red yellow in the color space approaches yellow in the color space.

4. The endoscope processor according to claim 1, wherein the processor is further configured to perform correction such that the first point and the second point are moved in different directions in the color space from each other when the second color is corrected to move the first point and the second point in the color space while maintaining the distance between the first point and the second point in the predetermined range.

5. An endoscope system comprising:
the endoscope processor according to claim 1; and
the endoscope.

6. The endoscope processor according to claim 1, wherein the processor is configured to perform the second image generation processing such that, in the color space, an angle formed by an axis connecting a center point and the first point before the correcting and an axis connecting the center point and the second point before the correcting is equal to an angle formed by an axis connecting the center point and the third point after the correcting and an axis connecting the center point and the fourth point after the correcting.

7. The endoscope processor according to claim 1,
wherein the first color is one of an average value, a mode value, an intermediate value, a maximum value and a minimum value of colors of pixels included in the first portion, and
wherein the second color is one of an average value, a mode value, an intermediate value, a maximum value and a minimum value of colors of pixels included in the second portion.

8. An endoscope system comprising:
a processor comprising hardware, the processor being connected to an endoscope configured to capture an image of return light of a first narrowband light and a second narrowband light from a subject to be examined, the first and second narrowband light being included in an observation target wavelength band ranging from a wavelength at which an absorption coefficient takes a local maximum value to a wavelength at which the absorption coefficient takes a local minimum value in a hemoglobin absorption characteristic of a living tissue, wherein the second narrowband light yields a lower absorption coefficient and a lower scattering coefficient by a living tissue than the first narrowband light, and to generate an image signal of the image,
wherein the processor is configured to:
  generate a first image in which the bleeding area is emphasized, from the image signal; and
  perform a second image generation processing of generating a second image, the second image generation processing comprising:
    identify a first color of a first portion of the first image and a second color of a second portion of the first image by associating the first color with a first point in a color space and the second color with a second point in the color space, the first color corresponding to the bleeding area within the subject, the second color corresponding to an area other than the bleeding area within the subject;
    correct the first color such that the first point associated with the first color is corrected to a third point associated with a color in the color space between hues of yellow and red-yellow; and
    correct the second color such that the second point associated with the second color is corrected to a fourth point in the color space, wherein a first distance between the first point and the second point in the color space is substantially equal to a second distance between the third point and the fourth point.

* * * * *